United States Patent [19]

Ishida et al.

[11] Patent Number: 6,124,243

[45] Date of Patent: *Sep. 26, 2000

[54] METHOD OF CONTROLLING GRAMINACEOUS WEEDS

[75] Inventors: Yasuo Ishida, Osaka; Kazunari Ohta, Tsukuba; Harutoshi Yoshikawa, Kyoto, all of Japan

[73] Assignee: Takeda Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/075,017

[22] Filed: Jun. 11, 1993

Related U.S. Application Data

[63] Continuation of application No. 07/760,392, Sep. 16, 1991, abandoned.

[30] Foreign Application Priority Data

Sep. 26, 1990 [JP] Japan ................. 2-258142

[51] Int. Cl.[7] .................................................. A01N 43/54
[52] U.S. Cl. ................................................... 504/215
[58] Field of Search ........................................... 504/215

[56] References Cited

U.S. PATENT DOCUMENTS 5,017,212  5/1991  Ishida et al. ............... 504/213
5,032,166  7/1991  Taylor ........................... 71/92
5,534,482  7/1996  Ishida et al. ............... 504/215

FOREIGN PATENT DOCUMENTS 0238070  9/1987  European Pat. Off. .
0301919  2/1989  European Pat. Off. .

*Primary Examiner*—S. Mark Clardy
*Attorney, Agent, or Firm*—Foley & Lardner

[57] ABSTRACT

A herbicide comprising the sulfonylurea derivatives of the formula (I):

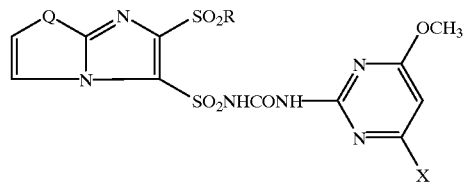

wherein Q is —CH=CH— or —S—, R is $C_{1-3}$ alkyl, and X is —$OCH_3$ or —$CH_3$; or a salt thereof, are useful for the control of undesired vegetation, for example, black glass (*Alopecurus myosuroides*) or downy brome (*Bromus tectorum L.*) in the presence of many valuable small grain cereals such as wheat, barley, oats and rye. The herbicide is also unexpectedly tolerant to small grain cereals such as wheat, barley, oats and rye.

1 Claim, No Drawings

METHOD OF CONTROLLING GRAMINACEOUS WEEDS

This application is a continuation of U.S. application Ser. No. 07/760,392 filed Sep. 16, 1991, now abandoned.

FIELD OF THE INVENTION

The present invention relates to novel herbicides and uses thereof for controlling weeds in farming of small grain cereals.

More specifically, the present invention relates to herbicides, which exert selectively controlling actions in the presence of many valuable small grain cereals such as wheat, barley, oats and rye.
Herbicides containing the compounds of the present invention are useful for the control of undesired vegetation, for example, graminaceous weeds (especially black grass (*Alopecurus myosuroides*) or downy brome (*Bromus tectorum L.*)).

The sulfonylurea derivatives of the present invention are especially active as herbicides for controlling undesired weeds in the presence of many valuable small grain cereals such as wheat, barley, oats and rye while being unexpectedly tolerant to small grain cereals such as wheat, barley, oats and rye.

BACKGROUND OF THE INVENTION

Various synthetic sulfonylurea compounds having herbicidal actions have been reported in Japanese Patent Application Laid Open Nos. 162587/1983 and 45572/1985, and European Patent Application Laid Open Nos. 96003, 152286 and 238,070. Several compounds are commercially available as herbicides for cereal areas (Glean™, Ally™, Harmony™, Amber™, etc.).

Although such sulfonylurea compounds exert potent herbicidal actions on broadleaf weeds in an extremely low concentration, they are still unsatisfactory in practical use because of drawbacks including either no or only weak herbicidal activity against graminaceous weeds in wheat fields under a selective use.

Therefore, it has been desired to develop a herbicide having a satisfying herbicidal activity against graminaceous weeds and no adverse effect such as damage of small grain cereals from the herbicide.

SUMMARY OF THE INVENTION

An aspect of the present invention is to provide a novel herbicide having advantageous activity against not only broadleaf weeds but also graminaceous weeds.

Another aspect of the present invention is to provide a novel herbicide exerting potent herbicidal activity against graminaceous weeds, specially black grass and downy brome, as well as broad herbicidal spectrum without adverse effect on many valuable small grain cereals such as wheat, barley, oats and rye. The herbicide is useful for controlling an undesired weed in a field of small grain cereals such as wheat, barley, oats and rye, especially wheat.

As a result of an extensive study, it has been discovered that compounds of the formula (I) and agriculturally acceptable salts thereof have unexpectedly potent herbicidal activity against a wide range of harmful weeds including not only broadleaf weeds such as cleaver (*Garium aparine*), wild chamomile (*Matricaria chamomilla*), wild violet (*Viola tricoloar*), chickweed (*Stellaria media*), wild mustard (*Sinapis arvensis L.*), and wild backwheat (*Polygonum convolvulus L.*) but also graminaceous weeds such as black grass, wild oat (*Avena fatua L*), downy brome and green foxtail (*Setaria viridis*), as well as exhibit substantially no adverse actions on small grain cereals. Among these, the compound and the salts thereof have strong herbicidal activity specially against graminaceous weeds (e.g., black grass, downy brome, wild chamomile, wild mustard, and chickweed), more specially against black grass and downy brome.

The present invention relates to a herbicide comprising an effective amount of a compound of the formula (I):

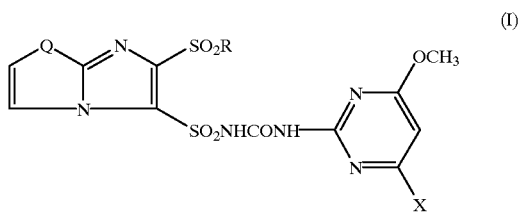

wherein Q is —CH=CH— or —S—, R is $C_{1-3}$ alkyl, and X is $OCH_3$ or $CH_3$; or an agriculturally acceptable salt thereof.

Further, the present invention relates to a herbicide for controlling graminaceous weeds (especially black grass and/or downy brome), which comprises an effective amount of the compound of the formula (I) or an agriculturally acceptable salt thereof.

Still further, the present invention relates to a method for combatting undesired plants in farming of small grain cereals, which comprises applying a herbicidally effective amount of the compound of the formula (I) or an agriculturally acceptable salt thereof or the composition containing the same to said plants.

In the foregoing formula, "$C_{1-3}$ alkyl" for R means straight or branched alkyl including, for example, methyl, ethyl, n-propyl, isopropyl, etc. Preferred examples of such alkyl are methyl and ethyl, more preferably ethyl.

X is methoxy or methyl, more preferably methoxy.

Q is —CH=CH— or —S—, more preferably —CH=CH—.

The compound (I) has an acidic group

The compound (I) can form a salt with an inorganic or organic base.

Examples of the agriculturally acceptable salts of the compounds [I] include salts with inorganic bases such as alkali metal (e.g. sodium, potassium, etc.), alkali earth metal (e.g. magnesium, calcium, etc.) and ammonia as well as organic bases such as dimethylamine, triethylamine, pyrrolidine, piperidine, piperazine, morpholine, benzylamine, ethanolamine and diethanolamine.

The compounds [I] or agriculturally acceptable salts thereof can be employed as herbicides in any application form suitable for conventional agricultural chemicals. For this purpose, a herbicidal composition comprising an effective amount of the compounds [I] or agriculturally acceptable salts thereof and an agriculturally acceptable vehicle can be prepared by admixing the compounds or salts thereof with the vehicle including a solid carrier, liquid medium, etc. For example, one or more species of these compounds [I] and agriculturally acceptable salts thereof can be dissolved or dispersed in a suitable agriculturally acceptable liquid or solid vehicle, or admixed with or adsorbed on a suitable agriculturally acceptable vehicle, for example, a solid carrier, according to purposes of use, to form a suitable formulation or preparation such as an emulsifiable concentrate, oil, water soluble solid, hydrate, wettable powder, dust, DL dust (drift-less dust), suspension concentrate, microgranule, microgranule F, granule, for example, water-dispersible granule, tablet, liquid, spray or aerosol. Among these, wettable powder, emulsifiable concentrate, flowable dust and granule are preferable. Wettable powder and emulsifiable concentrate are more preferable. These formulations can be prepared by any conventional method known per se. For example, they may contain, if necessary, an emulsifier, suspending agent, spreader, penetrant, wetting agent, thickener, mucilage, stabilizer, etc.

Suitable examples of the liquid vehicle or carrier (solvent) include water, alcohols (e.g. methanol, ethanol, n-propanol, isopropanol, ethylene glycol, etc.), ketones (e.g. acetone, methyl ethyl ketone, etc.), ethers (e.g. dioxane, tetrahydrofuran, ethylene glycol monomethyl ether, diethylene glycol monomethyl ether, propylene glycol monomethyl ether, etc.), aliphatic hydrocarbons (e.g. kerosene, lamp oil, fuel oil, machine oil, etc.), aromatic hydrocarbons (e.g. benzene, toluene, xylene, solvent naphtha, methylnaphthalene, etc.), halogenated hydrocarbons (e.g. dicholoromethane, chloroform, carbon tetrachloride, etc.), acid amides (e.g. dimethylformamide, dimethylacetamide, etc.), esters (e.g. ethyl acetate, butyl acetate, fatty acid glycerol ester, etc.), and nitriles (e.g. acetonitrile, propionitrile, etc.). These solvents may be used individually or in a suitable mixed form of two or more ingredients in a suitable ratio.

Examples of the solid carrier (diluent/extender) include vegetable powders (e.g. soybean meal, tobacco powder, wheat flour, sawdust, etc.), mineral powders (e.g. clays such as kaolin, bentonite, terra alba, talcs such as talcum powder and agalmatolite powder, and silicas such as diatomaceous earth and mica powder), alumina, sulfur powder, and active carbon. These solid carriers may be used individually or in a suitable mixed form of two or more ingredients in a suitable ratio.

The above-mentioned liquid or solid vehicles (or carriers) can be used independently in combination. An amount of the vehicle is in the range of up to 100 wt % to the whole composition.

The surfactants which can be employed as said emulsifier, spreading agent, penetrating agent or dispersing agent include various soaps and nonionic or anionic surface active agents such as polyoxyethylene alkyl aryl ethers [e.g. Noigen™ and E·A 142™, Dai-ichi Kogyo Seiyaku K.K.], polyoxyethylene allyl phenyl ether formaldehyde condensates [e.g. Newcalgen E-300™], polyoxyethylene phenyl phenol ether sulfates [e.g. Agrizol FL-2017™], special polyhydric polymers [e.g. Agrizol FL-104FA™], polyoxyethylene aryl ethers [e.g. Nonal™, Toho Kagaku K.K.], alkyl sulfates [e.g. Emal 10™ and Emal 40™, Kao K.K.], alkyl sulfonates [e.g. Neogen™ and Neogen T™, Dai-ichi Kogyo Seiyaku K.K.; Neopellex, Kao K.K.], polyoxyethylene glycol ethers [e.g. Nonipol 85™, Nonipol 100™ and Nonipol 160™, Sanyo Kasei K.K.], and polyhydric alcohol esters [e.g. Tween 20™ and Tween 80™, Kao K.K.]. An amount of the surfactant is in the range of 0 to 50 wt %, preferably 1 to 25 wt % to the whole composition.

The proportion of the active constituents in a herbicidal composition can vary according to intended uses. For example, an appropriate range is about 1 to 90 wt % in the case of an emulsifiable concentrate, wettable powder, suspension concentrate and water-dispersible granule, about 0.01 to 10 wt % in the case of oil, dust and DL dust, about 0.05 to 10 wt % in the case of microgranule, microgranule F, etc. The concentration of active ingredients may be changed according to intended uses. The emulsifiable concentrate, wettable powder and flowable dust are sprinkled after diluted or extended with water or the like (e.g. 100 to 100,000-fold).

The exact rate to be applied is dependent not only on a specific active ingredient being applied, but also on a particular action desired (e.g. general or selective control), the season, place and method of application, the cereal species, the plant species to be modified and the stage of growth thereof as well as the part of the plant to be contacted with the active ingredient. Preferably, the herbicide of the invention is employed, in general, in such a manner that the proportion of active ingredient (compound [I] and/or salt thereof) is in the range of 0.05 to 20 g, more preferably 0.1 to 5 g, per are.

The active ingredients of the present invention and herbicidal compositions containing the same are preferably applied to target plants by mixing into soils or fields prior to sowing, treating soils or fields before sprouting, sprinkling over stems and leaves of cereals directly, etc. in cereal areas.

The compound [I] and/or salt thereof can be used, as the case may be, in combination with other herbicides, plant growth regulators, fungicides (e.g. organochlorine fungicides, organosulfur fungicides, azole fungicides, antibiotics, etc.), pesticides (e.g. pyrethroid insecticides, organophosphorus insecticides, carbamate insecticides, etc.), acaricides, miticides, nematocides, plant hormones, synergists, attractants, repellents, pigments, fertilizers and manures.

As mentioned hereinbefore, a method for controlling an undesired weed in an upland field, comprising application of a herbicidally effective amount of the compound [I] or the agriculturally acceptable salt thereof to the field, is provided.

The upland field is specially for small grain cereals such as wheat, barley, oats and rye, more specially for wheat.

The undesired weed is of the same meaning as mentioned before. The amount of the compound [I] or the agriculturally acceptable salt thereof is also the same as mentioned before.

The compounds [I] and their salts of the present invention can be prepared by known methods per se, for example, Processes described below according to European Patent Application Laid Open No. 238,070 (Japanese Patent Laid Open No. 38091/1989).

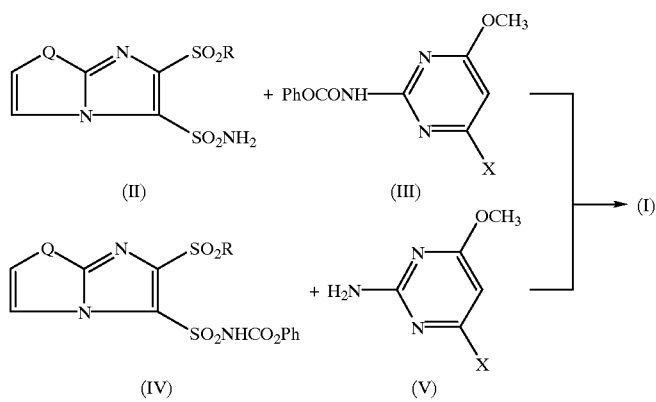

wherein each group has the same meaning as defined above.

The compound [II] or salt thereof is usually reacted with the compound [III] or salt thereof in the presence of a base (e.g. 1,8-diazabicyclo[5,4,0]undecene-7 ( hereinafter briefly referred as DBU), triethylamine, etc.) in an inert solvent such as acetonitrile and chloroform.

The compound [IV] or salt thereof is also reacted with the compound [V] or salt thereof in the same solvent as mentioned above.

The compounds [II], [IV] and their salts can be prepared by methods according to Japanese Patent Laid Open No. 316379/1989.

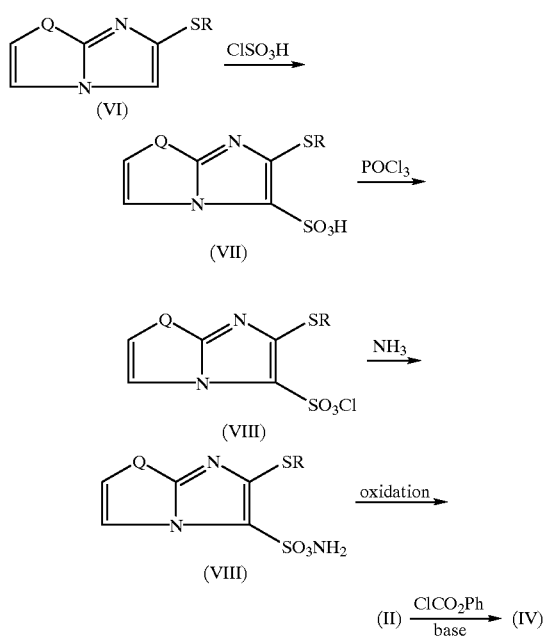

wherein each group has the same meaning as defined above.

In the above Processes, the intermediates [VII], [VIII], [IX], [II], or salt thereof may be employed for the subsequent reaction without isolation nor purification.

The starting compounds [VI] and their salts can be prepared either by or according to the method as described in European Patent Application Laid Open No. 238,070 (Japanese Patent Laid Open No. 38091/1989).

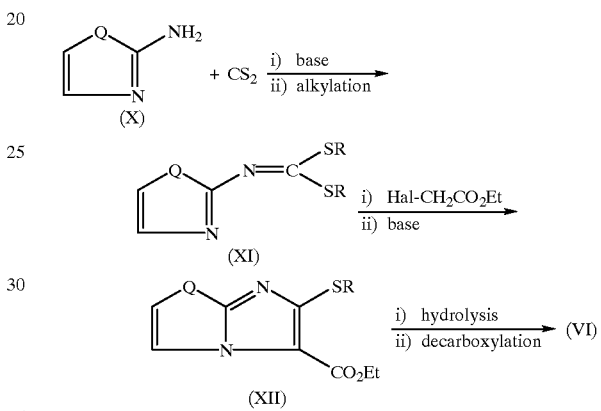

wherein each group has the same meaning as defined above.

The herbicides of the present invention have high herbicidal activity in an extremely small amount against a wide range of weeds in farming of small grain cereals.

The herbicides of the present invention are useful in controlling, specifically graminaceous weeds (more specifically black grass and downy brome, which were hardly removed in the prior art).

The herbicides of the present invention exert selectively controlling actions in the presence of many valuable small grain cereals such as wheat, barley, oats and rye.

The herbicides of the present invention are tolerant to mammalian animals, birds, fish and other water creatures.

The herbicides of the present invention can be employed safely without pollution to the environment.

The following reference, preparation examples, working examples and test examples are intended to illustrate the invention in further detail and should by no means be construed as limiting the scope of the invention.

The abbreviations used in the following Reference Examples, and Preparation Examples and Tables have the following meanings.

s: singlet, d: doublet, t: triplet, q: quartet, d.d: doublet of doublets, m: multiplet, br: broad, J: coupling constant, DMSO: dimethylsulfoxide, ph: phenyl.

%: wt %, unless specified.

The term "room temperature" means usually about 10–30° C.

Reference Example 1

6-Ethylthioimidazo[2,1-b]thiazole (a) To a suspension of sodium hydride (34.3 g, 60% in mineral oil) in dimethylformamide (1 l) was added 44.8 g of ethyl mercaptan dropwise under cooling and the mixture was stirred for 30 minutes at room temperature. Ethyl 6-mesylimidazo[2,1-b]thiazole-5-carboxlate (197.8 g) was gradually added to the resulting mixture in an small amount. After stirring for 3 hours at room temperature, the reaction mixture was poured into iced-water (3 l) and precipitated crystals were isolated by filtration, washed with water and dried to afford 161.3 g of ethyl 6-ethylthioimidazo[2,1-b]thiazole-5-carboxlate.

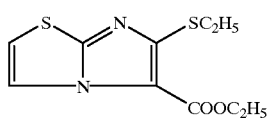

(b) To a solution of sodium hydroxide (414 g) in water (1.2 l) and ethanol (800 ml) was added 161.3 g of ethyl 6-ethylthioimidazo[2,1-b]thiazole-5-carboxlate and the mixture was heated under reflux for 1.5 hours. The ethanol was distilled off and the residue was diluted with water (2 l) and neutralized with hydrochloric acid (to pH=1). Precipitated crystals were isolated by filtration and washed with water. The wet crystals were heated at 150° C. for 30 minutes. During heating, the crystal formed effervescently an oil. The oil was dissolved in chloroform (500 ml), washed with aqueous sodium bicarbonate and dried over anhydrous sodium sulfate. Distillation of chloroform gave 115.4 g (yield, 86.8%) of the oily title compound.

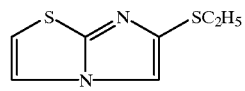

NMR(CDCl$_3$) δ: 1.28(t, 3H), 2.92(q, 2H), 6.83(d, 1H), 7.38(d, 1H), 7.48(s, 1H)

Reference Example 2

6-(n-Propylthio)imidazo[2,1-b]thiazole

In a manner similar to the procedure in Reference Example 1, the oily title compound was prepared from ethyl 6-mesylimidazo[2,1-b]thiazole-5-carboxlate and n-propyl mercaptan.

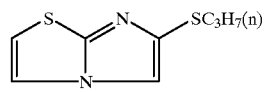

NMR(CDCl$_3$) δ: 1.00(t, 3H), 1.43–1.90(m, 2H), 2.88(t, 2H), 6.83(d, 1H), 7.38(s, 1H), 7.47(s, 1H)

Reference Example 3

6-Isopropylthioimidazo[2,1-b]thiazole

In a manner similar to the procedure in Reference Example 1, the oily title compound was prepared from ethyl 6-mesylimidazo[2,1-b]thiazole-5-carboxlate and isopropyl mercaptan.

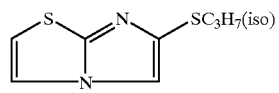

NMR(CDCl$_3$) δ: 1.30(s, 6H), 3.15–3.65(m, 1H), 6.85(d, 1H), 7.38(d, 1H), 7.62(s, 1H)

Reference Example 4

2-Isopropylthioimidazo[1,2-a]pyridine

In a manner similar to the procedure in Reference Example 1, the oily title compound was prepared from ethyl 2-mesylimidazo[1,2-a]pyridine-3-carboxlate and isopropyl mercaptan.

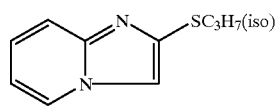

Reference Example 5

2-Ethylthioimidazo[1,2-a]pyridine-3-sulfonamide

To a solution of 2-ethylthioimidazo[1,2-a]pyridine (36.0 g, Japanese Patent Application Laid Open No. 38091/1989) in dichloroethane (50 ml) was added a solution of chlorosulfonic acid (28.0 g) in dichloroethane (300 ml) dropwise below 50° C. After addition, the mixture was heated under reflux with stirring for 7 hours and cooled followed by addition of triethylamine (27.0 g). The resultant mixture was stirred at room temperature for 30 minutes and then heated. Phosphorus oxychloride (37.2 g) was added to the mixture dropwise under reflux. Stirring was continued for 1.5 hours. After cooling, the reaction mixture was washed with water and the dichloroethane layer was concentrated in vacuo. The residue was dissolved in acetonitrile (300 ml) and stirred at room temperature for 1 hour after addition of aqueous ammonia (50 ml) at 10–20° C. under cooling.

The reaction mixture was concentrated in vacuo to an about half volume and precipitated crystals were isolated by filtration, washed with water and dried to afford 29.1 g (yield, 56.4%) of the title compound as a white crystal.

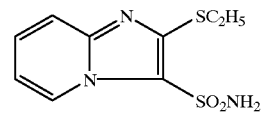

m.p. 169–171° C.

NMR(DMSO-d$_6$) δ: 1.35(t, 3H), 3.20(q, 2H), 7.05–7.25(m, 1H), 7.39–7.60(m, 1H), 7.66(d, 1H), 7.75(s, 2H), 8.60(d, 1H)

In a manner similar to the procedure in Reference Example 5, the following sulfonamide compounds as listed in Tables 1 and 2 were prepared.

TABLE 1

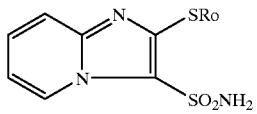

| Ro | NMR (DMSO-d$_6$) δ | m.p. (° C.) |
| --- | --- | --- |
| CH$_3$ | 2.58(s, 3H), 7.05–7.29(m, 1H), 7.39–7.60(m, 1H), 7.70(d, 1H), 7.75(s, 2H), 8.60(d, 1H) | 185–187 |
| n-C$_3$H$_7$ | 1.0(t, 3H), 1.50–1.96(m, 2H), 3.19(t, 2H), 7.01–7.27(m, 1H), 7.37–7.59(m, 1H), 7.69(d, 1H), 7.76(s, 2H), 8.64(d, 1H) | 153–155 |
| i-C$_3$H$_7$ | 1.40(d, 6H), 3.79–4.29(m, 1H), 7.08–7.29(m, 1H), 7.39–7.61(m, 1H), 7.70(d, 1H), 7.78(s, 2H), 8.64(d, 1H) | 141–143 |

TABLE 2

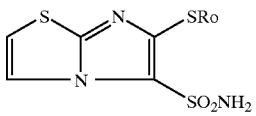

| Ro | NMR (DMSO-d$_6$) δ | m.p. (° C.) |
| --- | --- | --- |
| CH$_3$ | 2.52(s, 3H), 7.48(d, 1H), 7.92(d, 1H), 7.73(s, 2H), | 172–174 |
| C$_2$H$_5$ | 1.30(t, 3H), 3.10(q, 2H), 7.47(d, 1H), 7.72 (bd.s, 2H), 7.92(d, 1H) | 149–150 |
| n-C$_3$H$_7$ | 0.98(t, 3H), 1.30–1.95(m, 2H), 3.08(m, 2H), 7.48(d, 1H), 7.75(s, 2H), 7.93(d, 1H) | 138–141 |
| i-C$_3$H$_7$ | 1.33(t, 6H), 3.60–4.10(m, 1H), 7.47(d, 1H), 7.70(s, 2H), 7.93(d, 1H) | 136–139 |

TABLE 3

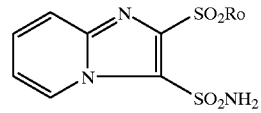

| Ro | NMR (DMSO-d$_6$) δ | m.p. (° C.) |
| --- | --- | --- |
| CH$_3$ | 3.45(s, 3H), 7.45(t, 1H), 7.58–7.90(m, 2H), 7.92(s, 2H), 8.96(d, 1H) | 214–216 |
| n-C$_3$H$_7$ | 1.0(t, 3H), 1.51–1.99(m, 2H), 3.56(t, 2H), 7.29–7.51(m, 1H), 7.58–7.80(m, 1H), 7.90(d, 1H), 7.94(s, 2H), 8.98(d, 1H) | 188–189 |
| i-C$_3$H$_7$ | 1.29(d, 6H), 3.70–4.20(m, 1H), 7.28–7.50(m, 1H), 7.58–7.79(m, 1H), 7.85(s, 2H), 7.90(d, 1H), 9.02(d, 1H) | 210–211.5 |

TABLE 4

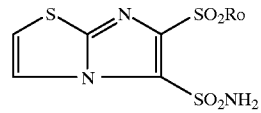

| Ro | NMR (DMSO-d$_6$) δ | m.p. (° C.) |
| --- | --- | --- |
| CH$_3$ | 3.35(s, 1H), 7.67(d, 1H), 7.77(s, 2H), 8.13(d, 1H), | 248–249 |
| C$_2$H$_5$ | 1.26(t, 3H), 3.47(q, 2H), 7.70(d, 1H), 7.72(d, 2H), 8.15(d, 1H) | 251–253 |
| n-C$_3$H$_7$ | 0.97(t, 3H), 1.45–1.95(m, 2H), 3.30–3.63(t, 2H), 7.30(d, 1H), 7.82(s, 2H), 8.15(d, 1H) | 252–254 |
| i-C$_3$H$_7$ | 1.27(d, 6H), 3.50–3.95(m, 1H), 7.75(d, 1H), 7.78(s, 2H), 8.15(d, 1H) | ~210 |

Reference Example 6

2-Ethylsulfonylimidazo[1,2-a]pyridine-3-sulfonamide

To a solution of 2-ethylthioimidazo[1,2-a]pyridine-3-sulfonamide (27.0 g) in dimethylformamide (300 ml) was added 45.0 g of m-chloroperbenzoic acid at 5–20° C. under cooling and the mixture was stirred at 5–20° C. for 3 hours.

The resultant mixture was poured into iced water (1.5 l) and precipitated crystals were isolated by filtration. The wet crystal was added to an aqueous sodium bisulfite solution (500 ml, NaHSO$_3$ 1.0 g), stirred at room temperature for 30 minutes, isolated by filtration, washed with aqueous sodium carbonate and then water and dried to afford 20.8 g (yield, 68.6%) of the title compound as a white crystal.

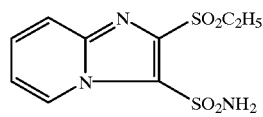

m.p. 190–192° C.
NMR(DMSO-d$_6$) δ: 1.23(t, 3H), 3.62(q, 2H), 7.30–7.58(m, 1H), 7.60–7.85(m, 1H), 7.95(d, 1H), 7.98(s, 2H), 9.0(d, 1H)

In a manner similar to the procedure in Reference Example 6, the following sulfonamide compounds as listed in Tables 3 and 4 were prepared.

Preparation Example 1

N-(2-Ethylsulfonylimidazo[1,2-a]pyridin-3-ylsulfonyl)-N-(4,6-dimethoxy-2-pyrimidinyl)urea (Compound No. 2)

To a suspension of 2-ethylsulfonylimidazo[1,2-a]pyridine-3-sulfonamide (20.5 g) and phenyl N-(4,6-dimethoxypyrimidin-2-yl)carbamate (20.0 g) in acetonitrile (250 ml) was added DBU (11.0 g) under ice-cooling and the mixture was stirred at room temperature for 3 hours.

The resultant mixture was poured into water (2 l), neutralized with hydrochloric acid (to pH 2 to 3) and precipitated crystals were isolated by filtration, washed with water and dried to afford 28.6 g (yield, 91.3%) of the title compound as a white crystal.

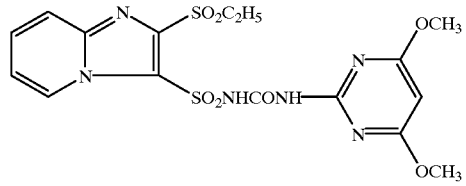

m.p. 197–199° C.
NMR(DMSO-d$_6$) δ: 1.29(t, 3H), 3.23(q, 2H), 3.95(s, 6H), 5.96(s, 1H), 7.11–7.31(m, 1H), 7.47–7.81(m, 2H), 8.92(d, 1H), 10.51(s, 1H), 12.91(s, 1H)

In a manner similar to the procedure in Preparation Example 1, the following sulfonylurea compounds as listed in Tables 5 and 6 were prepared.

TABLE 5

Structure: pyridine-fused imidazole with SO₂Ro, SO₂NHCONH-pyrimidine (OCH₃, Xo)

| Compound No. | Ro | Xo | NMR (DMSO-d₆) δ | m.p. (° C.) |
|---|---|---|---|---|
| 1 | CH₃ | OCH₃ | 3.49(s, 3H), 4.0(s, 6H), 5.98(s, 1H), 7.40–7.60 (m, 1H), 7.70–8.07(m, 2H), 9.29(d, 1H), 10.73 (s, 1H) | 203–205 |
| 3 | n-C₃H₇ | OCH₃ | 0.92(t, 3H), 1.42–1.89 (m, 2H), 3.52(t, 2H), 3.95(s, 6H), 5.97(s, 1H), 7.36–7.59(m, 1H), 7.67–8.0(m, 2H), 9.21 (d, 1H), 10.72(s, 1H), 13.02(s, 1H) | 184–189 |
| 4 | i-C₃H₇ | OCH₃ | 1.24(d, 6H), 3.80–4.03 (m, 1H), 3.95(s, 6H), 5.95(s, 1H), 7.36–7.59 (m, 1H), 7.67–7.99(m, 2H), 9.26(d, 1H), 10.71 (s, 1H) | 180–184 |

TABLE 6

Structure: thiazole-fused imidazole with SO₂Ro, SO₂NHCONH-pyrimidine (OCH₃, Xo)

| Compound No. | Ro | Xo | NMR (DMSO-d₆) δ | m.p. (° C.) |
|---|---|---|---|---|
| 5 | CH₃ | OCH₃ | 3.35(s, 3H), 3.97(s, 6H), 5.94(s, 1H), 7.79 (d, 1H), 8.23(d, 1H), 10.72(s, 1H) | 241–242 |
| 6 | C₂H₅ | OCH₃ | 1.20(t, 3H), 3.45(q, 2H), 3.97(s, 6H), 5.92 (s, 1H), 7.78(d, 1H), 8.22(d, 1H), 10.70(s, 1H), 13.15(bd.s, 1H) | 221–223 |
| 7 | CH₃ | CH₃ | 2.40(s, 3H), 3.33(s, 3H), 3.97(s, 3H), 6.60 (s, 1H), 7.72(d, 1H), 8.18(d, 1H), 11.00(s, 1H) | ~230 |
| 8 | C₂H₅ | CH₃ | 1.17(t, 3H), 2.45(s, 3H), 3.52(q, 2H), 3.98 (s, 3H), 6.62(s, 1H), 7.73(d, 1H), 8.22(d, 1H), 11.02(s, 1H) | 215–218 |
| 9 | n-C₃H₇ | OCH₃ | 0.92(t, 3H), 1.40(m, 2H), 3.43(t, 2H), 3.95 (s, 6H), 5.98(s, 1H), 7.80(d, 1H), 8.22(d, 1H), 10.78(s, 1H) | ~215 |

TABLE 6-continued

| Compound No. | Ro | Xo | NMR (DMSO-d₆) δ | m.p. (° C.) |
|---|---|---|---|---|
| 10 | i-C₃H₇ | OCH₃ | 1.18(d, 6H), 3.40–3.90 (m, 1H), 3.95(s, 6H), 5.98(s, 1H), 7.80(d, 1H), 8.22(d, 1H), 10.78 (s, 1H) | ~218 |

Test Example 1

Selectivity for Wheat (Preemergence Treatment)

Soil (about 300 g, steam sterilized soil) was packed into pots with 10 cm diameter and 20 seeds of undesired weeds (including 10 seeds of wild mustard) and 10 seeds of wheat were sown in separate respective pots followed by covering with soil to a thickness of about 1 cm. The test dilutions containing the compound [I] were sprayed on the soil surface of each of the pots at a rate of 1 or 0.25 g per are.

Each compound (1 or 0.25 g) to be utilized in a series of tests was dissolved in an acetone solution (500 ml) containing 2% by w/v of Tween™ 20 surfactant and diluted with water to 5 l of the final volume.

Four weeks after treatment, the herbicidal and adverse effects of the respective test ingredients used on respective groups of plants were visually evaluated by a comparison with the the control. The results are shown in Table 7. The experiments were carried out in a greenhouse. The degree of growth inhibition and damage was evaluated on the following scale (This scale was also employed in Test Example 2).

| Index | Activity | Inhibition (%) |
|---|---|---|
| 5 | Maximum (Dead) | 100 |
| 4 | Maximum | 99.9–87.6 |
| 3 | Strong | 87.5–75.1 |
| 2 | Moderate | 75.0–50.1 |
| 1 | Weak | 50.0–0.1 |
| 0 | None | 0 |

| Scale | Adverse Activity | Damage (%) |
|---|---|---|
| 0 | None | 0 |
| 1 | Very Little | 0.1–12.5 |
| 2 | Little | 12.6–25.0 |
| 3 | Moderate | 25.1–50.0 |
| 4 | Extensive | 50.1–99.9 |
| 5 | Extensive (Dead) | 100 |

Test Example 2

Selectivity for Wheat (Postemergence Treatment)

Soil (about 300 g, steam sterilized soil) was packed into pots with 10 cm diameter and 20 seeds of undesired weeds (including 10 seeds of wild mustard) and 10 seeds of wheats were sown in separate respective pots followed by covering with soil to a thickness of about 1 cm. When graminaceous weeds were at the 1 to 1.5 leaf stage, and broadleaf ones at the 2 to 6 leaf stage, 10 uniform seedlings were left while others were removed from each pot (except in the case of wild mustard, where 5 were left). When wheat was at the 2 to 3 leaf stage, 5 wheat plants were left in each pot. The test dilutions containing the compound [I] were sprayed on seedlings in each of the pots at a rate of 1 or 0.25 g per are.

Each compound (1 or 0.25 g) to be utilized in a series of tests was dissolved in an acetone solution (500 ml) containing 2% by w/v of Tween™ 20 surfactant and diluted with water to 5 l of the final volume. Four weeks after treatment, the herbicidal and adverse effects of the respective test ingredients used on respective groups of plants were evaluated in the same manner as in Test Example 1. The results are shown in Table 8. The experiments were carried out in a temperature-controlled greenhouse.

TABLE 7

(Preemergence Treatment)

| Compound No. | Dose (g/a) | Adverse Effect Wheat | Herbicidal Activity | | | | |
|---|---|---|---|---|---|---|---|
| | | | Black grass | Downy brome | Wild chamomile | Wild mustard | Chickweed |
| 1 | 0.25 | 0 | 4 | 3 | 5 | 5 | 4 |
| | 1.0 | 1 | 4 | 4 | 5 | 5 | 5 |
| 2 | 0.25 | 0 | 4 | 4 | 5 | 5 | 4 |
| | 1.0 | 1 | 5 | 4 | 5 | 5 | 5 |
| 3 | 0.25 | 0 | 3 | 3 | 4 | 4 | 3 |
| | 1.0 | 0 | 4 | 3 | 4 | 4 | 4 |
| 5 | 0.25 | 1 | 4 | 3 | 5 | 5 | 3 |
| | 1.0 | 1 | 5 | 3 | 5 | 5 | 4 |
| 6 | 0.25 | 0 | 4 | 3 | 5 | 5 | 4 |
| | 1.0 | 0 | 5 | 3 | 5 | 5 | 5 |
| 8 | 0.25 | 0 | 4 | 3 | 4 | 4 | 2 |
| | 1.0 | 0 | 4 | 3 | 4 | 4 | 4 |
| 10 | 0.25 | 0 | 4 | 2 | 4 | 4 | 3 |
| | 1.0 | 0 | 4 | 3 | 4 | 4 | 4 |
| (a) Comparative compound | 0.25 | 0 | 2 | 0 | 5 | 4 | 4 |
| | 1.0 | 1 | 2 | 0 | 5 | 4 | 5 |
| (b) Comparative compound | 0.25 | 1 | 1 | 0 | 5 | 2 | 3 |
| | 1.0 | 1 | 1 | 0 | 5 | 3 | 4 |

(a) Comparative compound: Glean ™
(b) Comparative compound: Harmony ™

TABLE 8

(Postemergence Treatment)

| Compound No. | Dose (g/a) | Adverse Effect Wheat | Herbicidal Activity | | | | |
|---|---|---|---|---|---|---|---|
| | | | Black grass | Downy brome | Wild chamomile | Wild mustard | Chickweed |
| 1 | 0.25 | 0 | 4 | 3 | 5 | 5 | 4 |
| | 1.0 | 1 | 4 | 4 | 5 | 5 | 5 |
| 2 | 0.25 | 0 | 4 | 4 | 5 | 5 | 5 |
| | 1.0 | 1 | 5 | 4 | 5 | 5 | 5 |
| 6 | 0.25 | 0 | 4 | 2 | 5 | 5 | 4 |
| | 1.0 | 0 | 5 | 3 | 5 | 5 | 4 |
| 8 | 0.25 | 0 | 4 | 3 | — | 5 | 4 |
| | 1.0 | 0 | 4 | 4 | — | 5 | 5 |
| 10 | 0.25 | 0 | 4 | 2 | — | 5 | 4 |
| | 1.0 | 0 | 4 | 3 | — | 5 | 4 |
| (a) Comparative compound | 0.25 | 1 | 2 | 0 | 5 | 5 | 5 |
| | 1.0 | 2 | 2 | 0 | 5 | 5 | 5 |
| (b) Comparative compound | 0.25 | 0 | 1 | 0 | 5 | 5 | 5 |
| | 1.0 | 2 | 2 | 0 | 5 | 5 | 5 |

(a) Comparative compound: Glean ™
(b) Comparative compound: Harmony ™

Example 1

Wettable Powders

| | |
|---|---|
| Compound No. 2 | 5 wt % |
| polyoxyethylene glycol ether (Nonipol 85 ™) | 3 wt % |
| sodium ligninsulfonate | 5 wt % |
| clay | 87 wt % |

The ingredients were well mixed and pulverized (The composition is suitably applied after dilution with water).

Example 2

Emulsifiable Concentrate

| | |
|---|---|
| Compound No. 3 | 2 wt % |
| xylene | 75 wt % |
| dimethylformamide | 18 wt % |
| polyoxyethylene glycol ether (Nonipol 85 ™) | 5 wt % |

The ingredients were well mixed (The composition is suitably applied after dilution with water).

Example 3

Suspension Concentrate

| | |
|---|---|
| Compound No. 6 | 2 wt % |
| polyoxyethylene allyl phenyl ether formaldehyde condesate (New Calgen E-300 ™) | 3 wt % |
| polyoxyethylene phenyl phenol ether sulfate (Agrizol FL-2017 ™) | 2 wt % |
| special polyhydric polymer (Agrizol FL-104FA ™) | 15 wt % |
| white carbon | 2 wt % |
| ethylene glycol | 10 wt % |
| water | 66 wt % |

The ingredients were mixed and wet pulverized to form suspended flowables (The composition is suitably applied after dilution with water).

Example 4

Granules

| | |
|---|---|
| Compound No. 1 | 0.2 wt % |
| sodium ligninsulfonate | 5 wt % |
| bentonite | 94.8 wt % |

The ingredients were mixed with water, kneaded and granulated.

Example 5

Wettable Powders

| | |
|---|---|
| Compound No. 2 | 10 wt % |
| Tween 20 ™ | 20 wt % |
| white carbon | 40 wt % |
| clay | 30 wt % |

The ingredients were well mixed and pulverized (The composition is suitably applied after dilution with water).

Example 6

Wettable Powders

| | |
|---|---|
| Compound No. 6 | 80 wt % |
| sodium dodecylbenzenesulfonate | 2 wt % |
| sodium naphthalenesulfonate | 3 wt % |
| clay | 15 wt % |

The ingredients were well mixed and pulverized (The composition is suitably applied after dilution with water).

What is claimed is:

1. A method for controlling a graminaceous weed selected from the group consisting of at least one of black grass and downy brome in an upland-field of wheat comprising applying to the field a herbicidally effective amount of the compound N-(2-ethylsulfonylimidazo[1,2-a]pyridin-3-ylsulfonyl)-N'-(4,6-dimethoxy-2-pyrimidinyl) urea or an agriculturally acceptable salt thereof.

* * * * *